United States Patent [19]

Kopolow et al.

[11] Patent Number: 5,182,098

[45] Date of Patent: Jan. 26, 1993

[54] TERPOLYMER HAIR FIXATIVES, AQUEOUS SOLUTION PROCESS FOR MAKING SAME AND WATER-BASED HAIR SPRAY FORMULATIONS WHICH MEET VOC STANDARDS

[75] Inventors: Stephen L. Kopolow, Plainsboro; Mohammed Tazi, Wayne; Edward W. Walls, Jr., Cranford, all of N.J.

[73] Assignee: ISP Investments Inc., Wilmington, Del.

[21] Appl. No.: 773,795

[22] Filed: Oct. 9, 1991

[51] Int. Cl.$^5$ .............................. A61K 7/11
[52] U.S. Cl. ........................ 424/47; 424/70; 424/71
[58] Field of Search .............................. 424/47, 70, 71

[56] References Cited

U.S. PATENT DOCUMENTS

| | | | |
|---|---|---|---|
| 4,057,533 | 11/1977 | Hort et al. | 526/264 |
| 4,521,404 | 6/1985 | Torenze et al. | 526/264 |
| 4,923,694 | 5/1990 | Shih et al. | 424/70 |
| 5,073,296 | 12/1991 | Kopolow et al. | 424/401 |

*Primary Examiner*—Thurman K. Page
*Assistant Examiner*—P. Kulkosky
*Attorney, Agent, or Firm*—Walter Katz; Marilyn J. Maue; Joshua J. Ward

[57] ABSTRACT

The present invention provides a terpolymer hair fixative comprising vinyl caprolactam, vinyl pyrrolidone and methacryloamidopropyl trimethylammonium chloride, an aqueous solution process for making such terpolymers, and water-based hair spray compositions which meet VOC standards.

9 Claims, No Drawings

TERPOLYMER HAIR FIXATIVES, AQUEOUS SOLUTION PROCESS FOR MAKING SAME AND WATER-BASED HAIR SPRAY FORMULATIONS WHICH MEET VOC STANDARDS

BACKGROUND OF THE INVENTION

1. Field of the Invention

This invention relates to polymeric hair fixatives, and, more particularly, to a terpolymer hair fixative, an aqueous solution process for making such terpolymers, and to water-based hair spray formulations which meet VOC standards.

2. Description of the Prior Art

Recent legislation in California and other states have mandated that hair sprays and other products must have low volatile organic chemicals (VOC) in the composition. Many useful hair fixatives, however, are compatible with alcohol or hydrocarbon solvents only. Accordingly, there is a need for water-based hair spray fixatives which can be formulated into hair spray compositions which can meet VOC regulations. Preferably it is desired to provide new and effective hair spray polymers or fixatives which can be prepared in aqueous medium, and thus can be formulated directly into water-based hair spray compositions which meet VOC requirements. Another object of the invention is to provide such compositions which exhibit good fixative properties, including effective substantivity, conditioning, hold and curl retention properties for the user.

SUMMARY OF THE INVENTION

The present invention provides a terpolymer hair fixative comprising vinyl caprolactam (VCL), vinyl pyrrolidone (VP) and methylacryloamidopropyl trimethylammonium chloride (MAPTAC) and an aqueous solution process for making such terpolymers so that the reaction product can be formulated directly into a water-based hair spray composition which meets VOC regulations.

DETAILED DESCRIPTION OF THE INVENTION

The terpolymer hair fixatives of the present invention suitably comprise about 5-70%, preferably 10 to 30%, by weight of vinyl caprolactam, about 25-90%, preferably 35 to 70%, by weight of vinyl pyrrolidone and about 5-20%, preferably 10 to 15%, by weight of methylacryloamidopropyl trimethylammonium chloride.

These terpolymers are conveniently prepared in aqueous solution by subjecting the above monomers, either in admixture or while being added sequentially into a reactor, to a temperature of about 40° to 120° C., preferably 60° to 70° C., under agitation in an inert atmosphere, for a period of about 0.5 to 10 hours, in the presence of a free radical polymerization initiator or catalyst. Representative catalysts include organic and inorganic peroxides, e.g. hydrogen peroxide, Lupersol 11, or an azo compound, e.g. azobisisobutyronitrile, 2,2'-azobis-(2,4-dimethyl valeronitrile); although others known in the art may be used as well. Ordinarily the aqueous solutions of the terpolymers thus-obtained are used as such for preparing water-based hair spray compositions which meet VOC regulations; however, if desired, the terpolymer product itself may be separated from the solution and recovered, for example, by evaporation of solvent, or other conventional method.

The invention will now be described with reference to the following examples.

EXAMPLES 1-17

Preparation of VCL/VP/MAPTAC Terpolymers in Aqueous Solution

A one-liter glass resin kettle, fitted with an anchor agitator, a temperature controller, a nitrogen inlet, a monomer feed tube and a condenser, was charged with VCL and distilled water. The solution in the kettle then was purged with nitrogen for 30 minutes with the dip tube was positioned at the bottom of the reactor. The nitrogen flow was continued and the dip tube was raised above the solution. The solution then was heated to 65° C. and a feed of VP/MAPTAC* monomers was pumped into the kettle at a rate such that the feed was completed in 2 hours. The start of addition of the feed was considered to be time zero. A first initiator charge of Lupersol 11 was added at time 10 minutes, a second shot of the same amount at 60 minutes, and the remaining third at the completion of the monomer feed. The total addition took approximately 20 minutes whereafter 0.8 g. of initiator had been added. The reaction mixture then was held at 65° C. for an additional 3 hours, heated to 90° C. and 1 g. of t-butyl perocctoate (Triganox 21) was added as an additional initiator. The reaction mixture was maintained at 90° C. for 8 hours, cooled and discharged.

* MAPTAC is available from The Virginia Carolina Chemicals Company as methacrylamidopropyl trimethylammonium chloride The several VCL/VP/MAPTAC terpolymers produced by this process are given in Table I below.

TABLE I

PREPARATION OF VCL/VP/MAPTAC TERPOLYMERS IN AQUEOUS SOLUTION

| EX. NO. | VCL (g) | VP (g) | MAPTAC* (g) | WATER** (g) | WEIGHT RATIO VCL/VP/MAPTAC |
|---|---|---|---|---|---|
| 1 | 5 | 90 | 5 | 455 | 5/90/5 |
| 2 | 10 | 85 | 5 | 455 | 10/85/5 |
| 3 | 15 | 80 | 5 | 455 | 15/80/5 |
| 4 | 20 | 75 | 5 | 455 | 20/75/5 |
| 5 | 5 | 90 | 10 | 460 | 5/85/10 |
| 6 | 5 | 90 | 10 | 460 | 5/85/10 |
| 7 | 10 | 85 | 10 | 460 | 10/80/10 |
| 8 | 15 | 80 | 10 | 460 | 15/75/10 |
| 9 | 20 | 75 | 10 | 460 | 20/70/10 |
| 10 | 5 | 80 | 15 | 465 | 5/80/15 |
| 11 | 5 | 80 | 15 | 465 | 5/80/5 |
| 12 | 10 | 75 | 15 | 465 | 10/75/15 |
| 13 | 10 | 75 | 15 | 465 | 10/75/15 |
| 14 | 15 | 70 | 15 | 465 | 15/70/15 |
| 15 | 15 | 70 | 15 | 465 | 15/70/15 |
| 16 | 20 | 65 | 15 | 465 | 20/65/20 |
| 17 | 20 | 65 | 15 | 465 | 20/65/15 |

*MAPTAC — added as 50% Aqueous Solution
**Water — Includes water in MAPTAC Solution The properties of the aqueous solutions of the VCL/VP/MAPTAC terpolymers produced above are presented in Table II below.

TABLE II

CHARACTERIZATION OF AQUEOUS SOLUTIONS OF VCL/VP/MAPTAC TERPOLYMERS

| EX. NO. | % SOLIDS | pH | RELATIVE VISCOSITY | % RESIDUAL VP |
|---|---|---|---|---|
| 1 | 20.04 | 4.81 | 2.51 | 0.0 |
| 2 | 20.11 | 4.13 | 2.07 | 0.0 |
| 3 | 17.73 | 3.95 | 2.01 | 0.0 |
| 4 | 24.41 | 3.96 | 2.41 | 0.02 |
| 5 | 19.48 | 4.62 | 3.39 | 0.0 |

TABLE II-continued
CHARACTERIZATION OF AQUEOUS SOLUTIONS OF VCL/VP/MAPTAC TERPOLYMERS

| EX. NO. | % SOLIDS | pH | RELATIVE VISCOSITY | % RESIDUAL VP |
|---|---|---|---|---|
| 6 | 21.87 | 4.21 | 3.56 | 0.02 |
| 7 | 20.20 | 4.48 | 4.13 | 0.02 |
| 8 | 22.41 | 5.02 | 4.31 | 0.03 |
| 9 | 20.02 | 5.18 | 4.22 | 0.0 |
| 10 | 24.08 | 5.67 | 5.98 | 0.015 |
| 11 | 20.09 | 4.34 | 5.41 | 0.0 |
| 12 | 19.10 | 5.53 | 4.79 | 0.015 |
| 13 | 17.66 | 4.46 | 4.56 | 0.0 |
| 14 | 18.38 | 5.05 | 4.53 | 0.01 |
| 15 | 22.87 | 4.45 | 5.45 | 0.0 |
| 16 | 20.00 | 4.91 | 3.24 | 0.0 |
| 17 | 17.45 | 4.55 | 4.50 | 0.0 |

As shown in Tables I and II, terpolymers containing three weight levels of MAPTAC were prepared, namely, 5%, 10%, and 15% by weight. At each concentration of MAPTAC, the VCL/VP ratio in the terpolymer was varied, the VCL content increasing from 5 to 20% by weight. For the series with 5% MAPTAC, the pH of the aqueous solution ranged from 3.95 to 4.81, the relative viscosity was 2.01 to 2.51, and the % VP residual was essentially zero. The pH for the series with 10% MAPTAC was 4.2 to 5.2, the relative viscosity was 3.56–4.31, and the % VP residual also was essentially zero. For the series with 15% MAPTAC, the pH range was 4.3 to 5.7; the relative viscosity was 3.24 to 5.98; residual VP again was absent from the product. Accordingly, increasing the % MAPTAC in the terpolymer resulted in an increase in the relative viscosity of the product, the pH remained essentially constant, and the residual VP content was essentially zero.

The water-based hair spray compositions of the invention containing the terpolymer hair fixative of VCL/VP/MAPTAC suitably comprises about 2 to 10%, preferably 3 to 6%, by weight of the terpolymer, about 10 to 60%, preferably 15 to 50%, by weight of water, about 20 to 40%, preferably 30 to 35%, by weight of dimethylether, and 0 to 15%, preferably 0 to 10%, by weight of ethanol. Such compositions are one-phase systems, can be made directly from the terpolymer solutions prepared by the aqueous solution process, meet VOC standards, and exhibit excellent performance characteristics in use as a hair spray.

While the mechanism of synergistic action of the three components of the terpolymer of the invention is not completely understood at present, it is believed that the presence of the VCL monomer therein provides a hydrophobic component which enhances the humidity resistance and hold of the hair spray composition while retaining the desired water solubility of the terpolymer and allowing its preparation by an aqueous solution process.

EXAMPLE 18
Preparation and Evaluation of Water-Based Hair Spray Compositions The following water-based hair spray formulations was prepared:

| | |
|---|---|
| Terpolymer solution 20% solids (Ex. 2) | 10 g. |
| Water-distilled | 45 |
| Ethanol-anhydrous | 10 |
| Dimethylether | 35 |
| | 100 g. |

The formulation was tested in the conventional manner for hold (curl retention at 90% RH and 80° F.) showed 85% average % curl retention after 90 minutes of treatment.

EXAMPLE 19

| | |
|---|---|
| Terpolymer solution (Exs. 2, 3 or 4) | 10 g. |
| Water-distilled | 55 |
| Dimethylether | 35 |
| | 100 g. |

These compositions showed a 70% curl retention after 90 minutes.

While the invention has been described with particular reference to certain embodiments thereof, it will be understood that changes and modifications may be made which are within the skill of the art. Accordingly, it is intended to be bound only by the following claims, in which:

What is claimed is:

1. A terpolymer hair fixative consisting essentially of about 5 to 20% by weight of vinyl caprolactam, about 65 to 90% by weight of vinyl pyrrolidone and about 5 to 15% by weight of methylacryloamidopropyl trimethylammonium chloride.

2. A terpolymer hair fixative according to claim 1 consisting essentially of about 10 to 15% by weight of vinyl caprolactam, about 70 to 85% by weight of vinyl pyrrolidone and about 10 to 15% by weight of methylacryloamidopropyl trimethylammonium chloride.

3. An aqueous solution of the terpolymer of claim 1 having a solids content of about 17 to 25%, a pH of about 4 to 6, a relative viscosity of about 2 to 6, and a residual vinyl pyrrolidone level of less than about 0.03%.

4. An aqueous solution according to claim 3 having a solids content of about 18 to 24%, a pH of about 4.2 to 5.5, a relative viscosity of about 3 to 5, and a residual vinyl pyrrolidone level which is essentially zero.

5. An aqueous solution process for preparing the terpolymers of claim 1 which comprises polymerizing the monomers in aqueous solution at a temperature of about 40° to 120° C., under agitation, in an inert atmosphere, for a period of about 0.5 to 10 hours, in the presence of a free radical polymerization initiator.

6. A one-phase, water-based hair spray composition consisting essentially of about 2 to 10% by weight of the terpolymer hair fixative of claim 1, about 10 to 60% by weight of water, about 20 to 40% by weight of dimethylether, and about 0 to 15% by weight of ethanol.

7. A one-phase, water-based hair spray composition according to claim 6 with about 3 to 6% by weight of the terpolymer hair fixative of claim 1, about 15 to 50% by weight of water, about 30 to 35% by weight of dimethylether, and about 0 to 10% by weight of ethanol.

8. A one-phase, water-based hair spray composition according to claim 6 in which the terpolymer hair fixative has the composition of claim 3.

9. A one-phase, water-based hair spray composition according to claim 6 which exhibits an average % curl retention of 70% to 85% after 90 minutes of hair treatment with said composition at 90% RH and 80° F.

* * * * *